(12) United States Patent
Granier et al.

(10) Patent No.: US 11,793,801 B2
(45) Date of Patent: Oct. 24, 2023

(54) TREATMENT OF PAIN AND NEUROLOGICAL CONDITIONS

(71) Applicant: BioCorRx, Inc., Anaheim, CA (US)

(72) Inventors: Brady J. Granier, Anaheim, CA (US); Jeffrey M. Witkin, Carmel, IN (US)

(73) Assignee: BIOCORRX PHARMACEUTICALS, INC., Anaheim, CA (US)

( * ) Notice: Subject to any disclaimer, the term of this patent is extended or adjusted under 35 U.S.C. 154(b) by 0 days.

(21) Appl. No.: 17/650,507

(22) Filed: Feb. 9, 2022

(65) Prior Publication Data

US 2022/0265627 A1 Aug. 25, 2022

Related U.S. Application Data

(63) Continuation of application No. PCT/US2021/061288, filed on Nov. 30, 2021.

(60) Provisional application No. 63/119,848, filed on Dec. 1, 2020, provisional application No. 63/119,837, filed on Dec. 1, 2020.

(51) Int. Cl.
*A61K 31/4468* (2006.01)
*A61P 25/36* (2006.01)

(52) U.S. Cl.
CPC ........ *A61K 31/4468* (2013.01); *A61P 25/36* (2018.01)

(58) Field of Classification Search
CPC ................................. A61K 31/4468
USPC ...................................... 514/329
See application file for complete search history.

(56) References Cited

U.S. PATENT DOCUMENTS

| 9,650,338 | B1 | 5/2017 | Martirosyan |
| 2018/0021322 | A1 | 1/2018 | Vardanyan et al. |
| 2020/0222380 | A1 | 7/2020 | Vardanyan et al. |
| 2022/0105081 | A1† | 4/2022 | Martirosyan |

OTHER PUBLICATIONS

Strang J., et al., "Opioid use disorder", Nat Rev Dis Primers (2020), 6, 3, pp. 1-28.
McDonald J., et al., "Opioid Receptors", Continuing Education in Anaesthesia, Critical Care & Pain (2014).
International Search Report of International Patent Application No. PCT/US2021/061288, dated Feb. 11, 2022.
Raise questions and answers (accessible at https://www.nimh.nih.gov/health/topics/schizophrenia/raise/raise-questions-and-answers (accessed Sept 9, 2022)).
Sivanesan et al., Opioid-induced Hallucinations: A Review of the Literature, Pathophysiology, Diagnosis, and Treatment, Anesth Analg., Oct. 2016; 123(4):836-843.
Yang et al., New Targets for Schizophrenia Treatment beyond the Dopamine Hypothesis, Int. J. Mol. Sci., 2017, 18(8), 1689.
Naloxone, Drugbank Online, (accessible at https://go.drugbank.com/drugs/DB01183 (accessed Sep. 15, 2022)).
Naloxone, Drugbank Online, (accessible at https://go.drugbank.com/drugs/DB00704 (accessed Sep. 15,2022)).
Feigenbaum et al., Effect of Naloxone on Dopamine Uptake and Release in vitro in the striatum, Neuropsychobiology, 1984; 11:94-97.
Jayaram-Lindström et al., Naltrexone modulates dopamine release following chronic, but not acute amphetamine administration: a translational study, Translational Psychiatry, (2017) 7, e1104.
U.S. Appl. No. 63/380,189, filed Oct. 19, 2022 First Named Inventor: Brady J. Granier BioCorRx Pharmaceuticals, Inc.
Ockert, David M., et al. "A nonopioid procedure for outpatient opioid detoxification." Journal of addiction medicine 5.2 (2011): 110-114.
Depression, National Institute of Mental Health, Sep. 2022. Retrieved Jan. 19, 2023, from https://www.nimh.nih.gov/health/topics/depression.
Watson et al., Effects of Naloxone on Schizophrenia: Reduction in Hallucinations in a Subpopulation of Subjects, Science, vol. 201, Jul. 7, 1978, pp. 73-76.†

(Continued)

*Primary Examiner* — Taofiq A Solola
(74) *Attorney, Agent, or Firm* — Maschoff Brennan; Brent A. Johnson; David W. Old

(57) ABSTRACT

The present disclosure is directed toward uses of compound 1 (or its stereoisomers) and compositions and/or dosage forms containing compound 1:

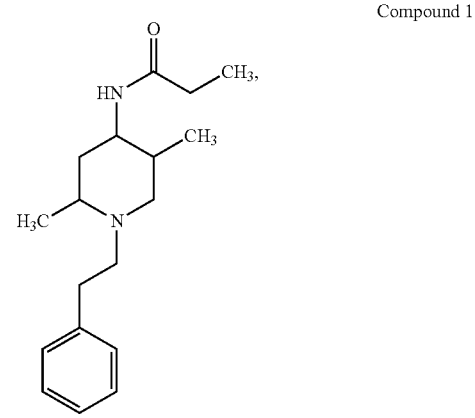

Compound 1 or a pharmaceutically acceptable salt thereof. Some uses of Compound 1 and/or its stereoisomers include treating a variety of diseases and disorders, including pain, depression, and schizophrenia. In some embodiments, Compound 1 and/or its stereoisomers may be useful in the treatment of a substance use disorder while inducing fewer withdrawal symptoms than a standard-of-care opioid addiction treatment.

10 Claims, No Drawings

(56) References Cited

OTHER PUBLICATIONS

Clark et al., The Role of the Role of Dynorphin and the Kappa Opioid Receptor in the Symptomatology of Schizophrenia: A Review of the Evidence, Biological Psychiatry, Oct. 1, 2019; 86:502-511.†
Bisaga et al., Antagonists in the Medical Management of Opioid Use Disorders: Historical and Existing Treatment Strategies, The American Journal on Addictions, 27: pp. 177-187, 2018.†
Mischoulon et al., Randomized, proof-of-concept trial of low dose naltrexone for patients with breakthrough symptoms of major depressive disorder on antidepressants, Journal of Affective Disorders, vol. 208, Jan. 15, 2017, pp. 6-14.†
Maurice et al., The Pharmacology of Sigma-1 Receptors, Pharmacol Ther. Nov. 2009, 124(2): 195-206.†
Park et al., Low-dose naltrexone in treating fibromyalgia and major depressive disorder, Clinical and Experimental Psychology 2019, vol. 5.†
Noon et al., A novel glial cell inhibitor, low dose naltrexone, reduces pain and depression, and improves function in chronic pain: A CHOIR study, The Journal of Pain, vol. 17, Issue 4, Supplement, S79 Apr. 2016.†
Kim et al., Curr. Pain Headache Rep., pp. 1-8, Aug. 26, 2020, Springer, published online.†

† cited by third party

TREATMENT OF PAIN AND NEUROLOGICAL CONDITIONS

CROSS REFERENCE TO RELATED APPLICATIONS

This application is a continuation application of International Patent Application No. PCT/US2021/061288, filed Nov. 30, 2021, which claims the benefit of U.S. Provisional Patent Application No. 63/119,848, filed Dec. 1, 2020, and Provisional Patent Application No. 63/119,837, filed Dec. 1, 2020; all of the above applications, U.S. patents issued from, or U.S. publications of any of the above applications are incorporated by reference in their entirety.

BACKGROUND

Opium is one of the world's oldest drugs. Opium derivatives morphine and codeine are among the most used clinical drugs to relieve severe pain, but addiction to and abuse of these medicines have inspired research into new pain relievers lacking side effects. The search for novel modulators of opioid receptors, particularly those that may be non-addictive or that do not bring about withdrawal symptoms, are an active area of unmet medical need.

SUMMARY

The present disclosure includes pharmaceutical compositions or dosage forms (including sustained release dosage forms) comprising compound 1, or enantiomers or diastereomers thereof, for the treatment and/or prevention of diseases and disorders. Compound 1 modulates various opioid receptors and may be useful in the treatment of various medical disorders and diseases.

Some embodiments include a method of treating a disease or disorder, comprising administering compound 1 to a human being in need thereof, wherein compound 1 is represented by the formula:

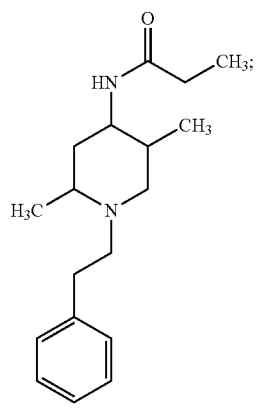

Compound 1 or a pharmaceutically acceptable salt thereof, wherein the disease or disorder is pain, depression, schizophrenia, obesity or weight-gain, or a substance use disorder; wherein for the treatment of a substance use disorder, compound 1 induces fewer withdrawal symptoms than a standard-of-care opioid addiction treatment.

Some embodiments include a dosage form comprising compound 1:

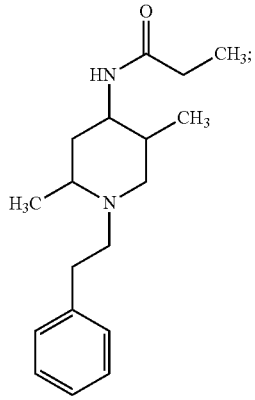

Compound 1 or a pharmaceutically acceptable salt thereof, wherein the dosage form is formulated for sustained release of compound 1.

Some embodiments include a dosage form comprising:

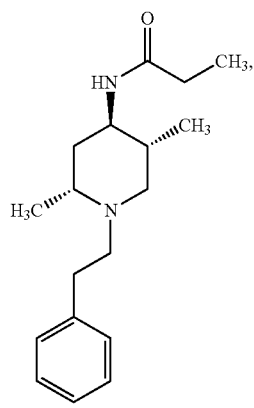 [SMILES: CCC(=O)N[C@@H]1C[C@@H](C)N(CCc2ccccc2)C[C@H]1C]

or a pharmaceutically acceptable salt thereof, having an enantiomeric excess of at least 50%, at least 60%, at least 70%, at least 80%, at least 90%, at least 95%, or at least 99%.

Some embodiments include a dosage form comprising:

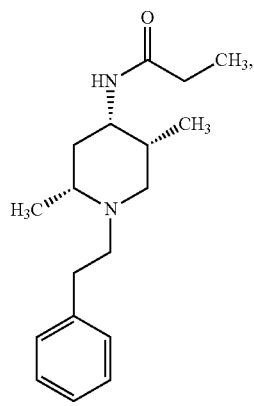 [SMILES: CCC(=O)N[C@H]1C[C@@H](C)N(CCc2ccccc2)C[C@H]1C]

or a pharmaceutically acceptable salt thereof, having an enantiomeric excess of at least 50%, at least 60%, at least 70%, at least 80%, at least 90%, at least 95%, or at least 99%.

Some embodiments include a dosage form comprising:

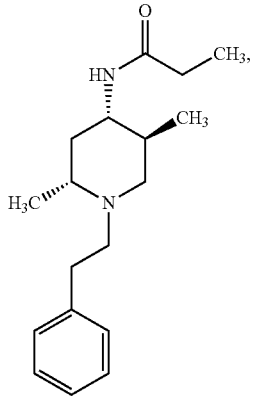 [SMILES: CCC(=O)N[C@H]1C[C@@H](C)N(CCc2ccccc2)C[C@@H]1C]

or a pharmaceutically acceptable salt thereof, having an enantiomeric excess of at least 50%, at least 60%, at least 70%, at least 80%, at least 90%, at least 95%, or at least 99%.

Some embodiments include a dosage form comprising:

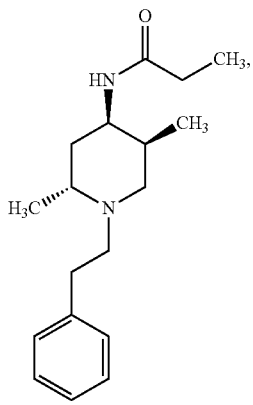 [SMILES: CCC(=O)N[C@@H]1C[C@@H](C)N(CCc2ccccc2)C[C@@H]1C]

or a pharmaceutically acceptable salt thereof, having an enantiomeric excess of at least 50%, at least 60%, at least 70%, at least 80%, at least 90%, at least 95%, or at least 99%.

Some embodiments include a dosage form comprising:

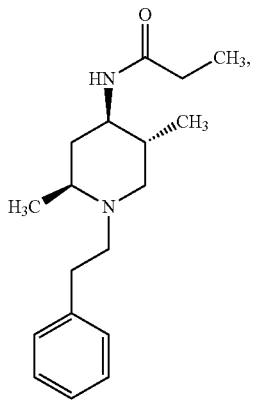 [SMILES: CCC(=O)N[C@@H]1C[C@H](C)N(CCc2ccccc2)C[C@H]1C]

or a pharmaceutically acceptable salt thereof, having an enantiomeric excess of at least 50%, at least 60%, at least 70%, at least 80%, at least 90%, at least 95%, or at least 99%.

Some embodiments include a dosage form comprising:

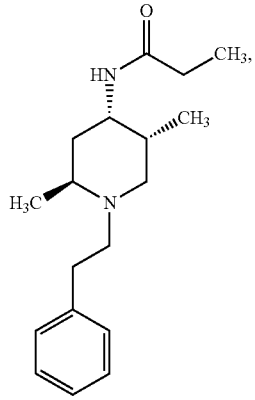 [SMILES: CCC(=O)N[C@H]1C[C@H](C)N(CCc2ccccc2)C[C@H]1C]

or a pharmaceutically acceptable salt thereof, having an enantiomeric excess of at least 50%, at least 60%, at least 70%, at least 80%, at least 90%, at least 95%, or at least 99%.

Some embodiments include a dosage form comprising:

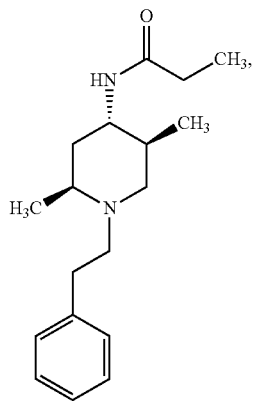 [SMILES: CCC(=O)N[C@H]1C[C@H](C)N(CCc2ccccc2)C[C@@H]1C]

or a pharmaceutically acceptable salt thereof, having an enantiomeric excess of at least 50%, at least 60%, at least 70%, at least 80%, at least 90%, at least 95%, or at least 99%.

Some embodiments include a dosage form comprising:

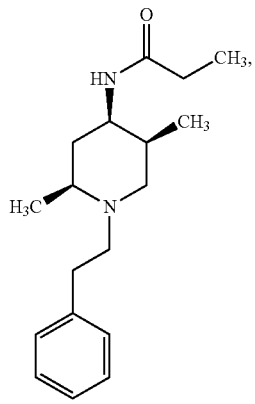 [SMILES: CCC(=O)N[C@@H]1C[C@H](C)N(CCc2ccccc2)C[C@@H]1C]

or a pharmaceutically acceptable salt thereof, having an enantiomeric excess of at least 50%, at least 60%, at least 70%, at least 80%, at least 90%, at least 95%, or at least 99%.

Some embodiments include a method of treating a disease or disorder, comprising administering a dosage form described herein to a mammal in need thereof.

DETAILED DESCRIPTION

Compound 1 has the general formula shown below.

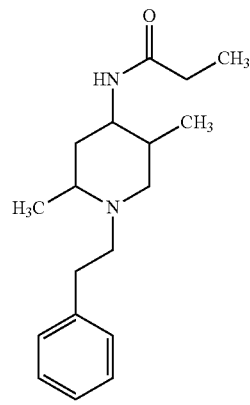

Compound 1

Compound 1 is known as 1-(2-phenylethyl)2,5-dimethyl-4-propionilaminopiperidine, or N-[2,5-dimethyl-1-(2-phenylethyl)piperidin-4-yl]propanamide, or 2,5-dimethyl-1-(2-phenyl)ethyl-4-propionilaminopiperidine or N-(2,5-dimethyl-1-phenethylpiperidin-4-yl)propionamide.

Compound 1 is chiral, bearing three stereogenic centers. The eight individual enantiomers of compound 1 are depicted below:

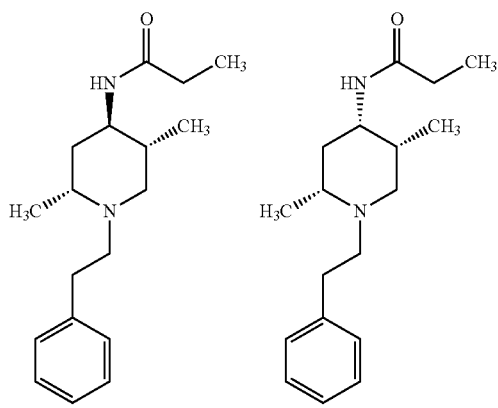

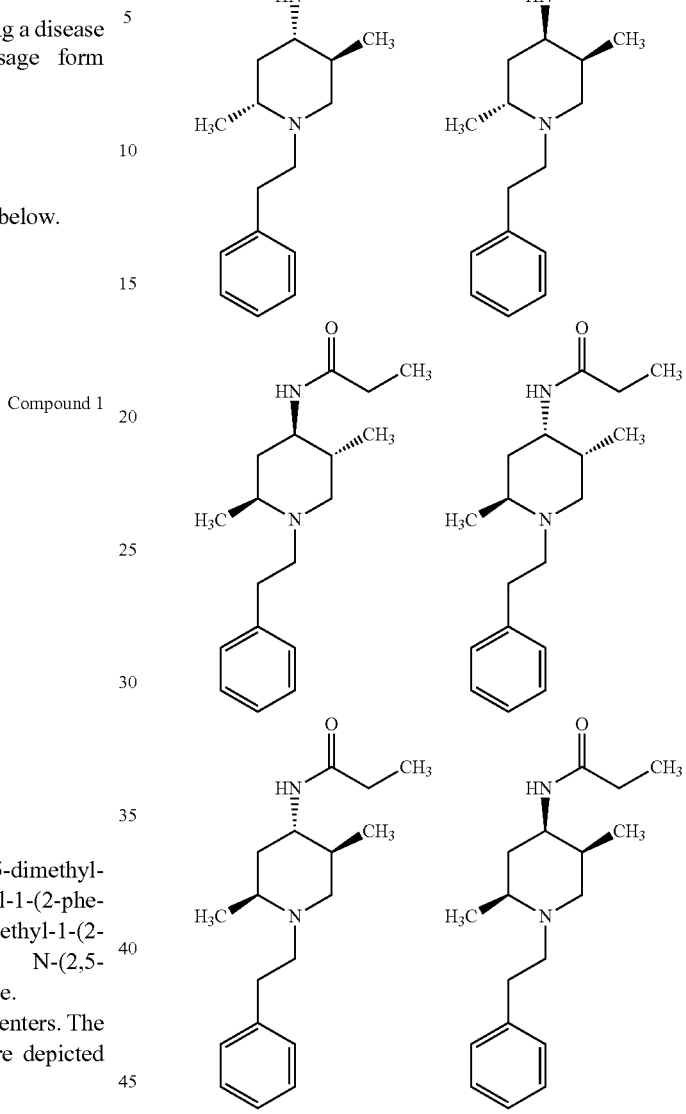

All isomers, diastereomers, and mixtures of the individual enantiomers of compound 1 are contemplated herein for use in pharmaceutical compositions, dosage forms (including sustained release dosage forms, or implants (including sustained release implants) for the treatment of diseases and disorders.

Unless otherwise indicated, any reference to a compound 1 herein, by structure, name, or any other means, includes pharmaceutically acceptable salts; alternate solid forms, such as polymorphs, solvates, hydrates, etc.; tautomers; deuterium-modified compounds, such as deuterium modified compound 1; or any chemical species that may rapidly convert to a compound described herein under conditions in which the compounds are used as described herein.

A "pharmaceutically acceptable salt" retains the desirable biological activity of compound 1, or an enantiomer or a diastereomer thereof, without unacceptable toxicological effects. Salts can be salts with a suitable acid, including, but not limited to, hydrochloric acid, hydrobromic acid, sulfuric acid, phosphoric acid, nitric acid and the like; acetic acid, oxalic acid, tartaric acid, succinic acid, malic acid, benzoic acid, pamoic acid, alginic acid, methanesulfonic acid, naphthalenesulphonic acid, and the like. Also included are salts of other acids such as salts with trifluoroacetic acid, chloroacetic acid, and trichloroacetic acid.

"Opiate" is a specific term that is used to describe drugs (natural and semi-synthetic) derived from the juice of the opium poppy. For example, morphine is an opiate but fentanyl (a completely synthetic drug) is not. "Opioid" is a general term that includes naturally occurring, semi-synthetic, and synthetic drugs, which produce their effects by combining with opioid receptors and are competitively antagonized by naloxone. For the purposes of this disclosure, the term opioid refers to opioid agonists, opioid antagonists, opioid peptides, and opioid receptors.

Superficially, compound 1 resembles the structure of fentanyl, which is a well-known pain medication and a very potent opioid receptor agonist. Compound 1, in contrast, was found to be a potent antagonist of the effects of fentanyl (respiratory depression and analgesia) that are induced by fentanyl through the mu opiate receptor. Further in vitro analyses have shown that compound 1 has a unique pharmacological profile. Specifically, compound 1 is found to be a partial agonist of mu opiate (MOP) receptors, an antagonist at kappa (KOP) and ORL1 (NOP) receptors, with further activity at sigma opiate sites. A potentially important property of partial agonists is that they display both agonistic and antagonistic effects. In the presence of a full agonist, a partial agonist will act as an antagonist, competing with the full agonist for the same receptor and thereby reducing the ability of the full agonist to produce its maximum effect. It is believed that the antagonistic nature of compound 1 at the ORL1 receptor may distinguish its activity in the context of existing medicines. A summary of the in vitro pharmacology of compound 1 in relation to common standard-of-care medications for opioid intoxication is shown below in Table 1.

thereof, is used in combination with another drug. In some embodiments, compound 1, or an enantiomer or a diastereomer thereof, and another drug or active pharmaceutical ingredient are both present in the subject dosage form. In some embodiments, compound 1, or an enantiomer or a diastereomer thereof, is used without opioids.

A subject dosage form may contain about 0.01 mg to about 1000 mg, 0.01-0.1 mg, 0.1-0.2 mg, 0.2-0.3 mg, 0.3-0.4 mg, 0.4-0.5 mg, 0.5-0.6 mg, 0.6-0.7 mg, 0.7-0.8 mg, 0.8-0.9 mg, 0.9-1 mg, about 1-2 mg, about 2-3 mg, about 3-4 mg, about 4-5 mg, about 5-6 mg, about 6-7 mg, about 7-8 mg, about 8-9 mg, about 9-10 mg, about 10-11 mg, about 11-12 mg, about 12-13 mg, about 13-14 mg, about 14-15 mg, about 15-16 mg, about 16-17 mg, about 17-18 mg, about 18-19 mg, about 19-20 mg, about 20-22 mg, about 22-24 mg, about 24-26 mg, about 26-28 mg, about 28-30 mg, about 30-32 mg, about 32-34 mg, about 34-36 mg, about 36-38 mg, about 38-40 mg, about 40-42 mg, about 42-44 mg, about 44-46 mg, about 46-48 mg, about 48-50 mg, about 50-55 mg, about 55-60 mg, about 60-65 mg, about 65-70 mg, about 70-75 mg, about 75-80 mg, about 80-85 mg, about 85-90 mg, about 90-95 mg, about 95-100 mg, about 100-110 mg, about 110-120 mg, about 120-130 mg, about 130-140 mg, about 140-150 mg, about 150-160 mg, about 160-170 mg, about 170-180 mg, about 180-190 mg, about 190-200 mg, about 200-300 mg, about 300-400 mg, about 400-500 mg, about 500-600 mg, about 600-700 mg, about 700-800 mg, about 800-900 mg, about 900-1000 mg, about 10-200 mg, about 10-100 mg, 200-500 mg, about 500-1000 mg, or about 200 mg, about 300 mg, about 400 mg, about 1000 mg, or any amount in a range bounded by any of these values, of compound 1, or an enantiomer or a diastereomer thereof, in a free base form or a salt form.

Data obtained from cell culture assays or animal studies can be used in formulating a range of dosage for use in humans. If the medicament is provided systemically, the dosage of such compounds lies preferably within a range of circulating concentrations that include the $IC_{50}$ or $EC_{50}$ with

TABLE 1

| Cmpd | Receptor | | | | |
|---|---|---|---|---|---|
| | Mu (MOP) | Kappa (KOP) | Delta (DOP) | ORL1 (NOP) | Sigma |
| Compound 1 | Partial agonist | Antagonist | Antagonist but weak | Antagonist | High Affinity |
| Buprenorphine | Partial agonist | Antagonist | Antagonist but weak | Agonist | High Affinity |
| Naloxone | Antagonist | Antagonist | Antagonist | Weak | Weak |
| Naltrexone | Antagonist | Antagonist but weak | Antagonist but weak | Weak | Weak |

Compound 1 also displays in vitro antagonistic activity at adrenergic receptors Alpha 1B, 2B and 2C, histamine H1 receptor, cholinergic muscarinic receptors 1, 3, 4, and 5, dopamine D4 receptor, and serotonin receptors 1A and 1B.

A pharmaceutical composition or dosage form (including a sustained release dosage form) comprising compound 1 or one of the individual stereoisomers depicted herein, (referred to hereafter collectively as "subject dosage form") may be used alone or in combination with other drugs for the treatment of various conditions. In some embodiments, compound 1, or an enantiomer or a diastereomer thereof, is used alone and/or compound 1, or an enantiomer or a diastereomer thereof, is the only drug or active pharmaceutical ingredient in the subject dosage form. In some embodiments, compound 1, or an enantiomer or a diastereomer little or no toxicity. The dosage may vary within this range depending upon the dosage form employed and the route of administration utilized. For any compound used in the method described herein, the therapeutically effective dose can be estimated initially from cell culture assays. A dose may be formulated in animal models to achieve a circulating plasma concentration or within the local environment to be treated in a range that includes the IC50 (i.e., the concentration of the test compound that achieves a half-maximal inhibition of an opiate receptor) as determined in cell culture. Such information can be used to more accurately determine useful doses in humans. Levels in plasma may be measured, for example, by liquid chromatography coupled to mass spectrometry. In some embodiments, a modulating effect is achieved with an IC50 less than 100 µM, 50 µM, 30 µM, 20 µM, 10 µM, 5 µM, or 1 µM.

An "effective amount" is an amount sufficient to effect beneficial or desired results. For example, a therapeutic amount is one that achieves the desired therapeutic effect. This amount can be the same or different from a prophylactically effective amount, which is an amount that prevents onset of disease or disease symptoms.

For the purposes of this disclosure, the term "treat," "treating," or a similar term, includes cure, mitigation, treatment, or prevention of disease in man or other animals, or any other effect that would be associated with a "drug" as defined under 21 USC 321(g).

In some embodiments, administration of compound 1, or an enantiomer or a diastereomer thereof, may occur one or more times per day. Some embodiments include administration of compound 1, or an enantiomer or a diastereomer thereof, once per day, twice per day, three times per day, or four times per day. Administration of compound 1, or an enantiomer or a diastereomer thereof, may occur one or more times for a single day, or for at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 30, at least 35, at least 40, at least 45, at least 50, at least 55, at least 60, at least 65, at least 70, at least 75, at least 80, at least 85, at least 90, at least 100, or more consecutive days. In some embodiments, administration of compound 1, or an enantiomer or a diastereomer thereof, may occur for up to about 7 days, up to about 14 days, up to about 1 month, up to about 6 months, up to about 1 year, up to about 2 years, up to about 5 years, up to about 10 years, up to about 20 years, up to about 50 years, or up to about 100 years. In some embodiments, administration of compound 1, or an enantiomer or a diastereomer thereof, is at least daily for at least two consecutive days. In some examples, administration of compound 1, or an enantiomer or a diastereomer thereof, is at least daily for at least seven consecutive days. Some embodiments include administration of compound 1, or an enantiomer or a diastereomer thereof, is at least daily for at least 14 consecutive days. In some cases, compound 1, or an enantiomer or a diastereomer thereof, is administered at least for 30 consecutive days.

A subject dosage form may contain a pharmaceutical carrier selected on the basis of the chosen route of administration and standard pharmaceutical practice as described, for example, in Remington's Pharmaceutical Sciences, 2005. The relative proportions of active ingredient and carrier may be determined, for example, by the solubility and chemical nature of the compounds, chosen route of administration and standard pharmaceutical practice.

Therapeutic compounds may be administered by any means that may result in the contact of the active agent (compound 1, or an enantiomer or a diastereomer thereof) with the desired site or site(s) of action in the body of a patient. The compounds may be administered by any conventional means available for use in conjunction with pharmaceuticals, either as individual therapeutic agents or in a combination of therapeutic agents. For example, compound 1, or an enantiomer or a diastereomer thereof, may be administered as the sole active agent in a pharmaceutical composition, or compound 1, or an enantiomer or a diastereomer thereof, can be used in combination with other therapeutically active ingredients. In some embodiments, compound 1, or an enantiomer or a diastereomer thereof, is administered without an opioid and/or the dosage form containing compound 1, or an enantiomer or a diastereomer thereof, does not also contain an opioid.

Compound 1, or an enantiomer or a diastereomer thereof, may be administered to a human patient in a variety of forms adapted to the chosen route of administration, e.g., orally or parenterally. Parenteral administration in this respect includes administration by the following routes: intravenous, intramuscular, subcutaneous, intraocular, intrasynovial, transepithelial including transdermal, sublingual and buccal; topically including dermal, rectal, and nasal inhalation via insufflation or aerosol.

Some subject dosage forms are sustained release dosage forms comprising compound 1, or an enantiomer or a diastereomer thereof. In some embodiments, the sustained release dosage form is a dermal patch. In other examples, the sustained release dosage form is a transdermal patch. Some embodiments include a sustained release viscous liquid or gel formulation of compound 1, or an enantiomer or a diastereomer thereof. In some embodiments, compound 1, or an enantiomer or a diastereomer thereof, is formulated as a solid implant to be implanted subcutaneously or into some other tissue.

In some embodiments, the sustained release dosage form is a nasal spray. In some embodiments, the sustained release dosage form is a sublingual pill. In some embodiments, the sustained release dosage form is a sublingual spray. In some embodiments, the sustained release dosage form is a sublingual strip. In some embodiments, the sustained release dosage form is an intramuscular injection. In some embodiments, the sustained release dosage form is an intramuscular implant. In some embodiments, the sustained release dosage form is a subcutaneous injection. In some embodiments, the sustained release dosage form is a subcutaneous implant.

Transdermal patches may have many components which may include, but are not limited to: a liner that protects the patch during storage and is removed prior to use; compound 1, or an enantiomer or a diastereomer thereof, which may be present in a reservoir, in direct contact with release liner; an adhesive to adhere the components of the patch together along with adhering the patch to the skin; a membrane that controls the release of compound 1, or an enantiomer or a diastereomer thereof, from the reservoir and/or in multi-layer patches; a backing that protects the patch from the outer environment; a permeation enhancer which enhances the penetration of compound 1, or an enantiomer or a diastereomer thereof, thereby increasing delivery of drug; a matrix filler which provides bulk to the matrix, and in some examples serving as matrix stiffening agents; a stabilizer or stabilizers, including anti-oxidants, preservatives etc.

In some embodiments, transdermal patches may comprise a single-layer drug-in-adhesive comprising compound 1, or an enantiomer or a diastereomer thereof. In some embodiments of this single-layer transdermal patch, the adhesive layer not only serves to adhere the various layers together, along with the entire system to the skin, but is also responsible for releasing compound 1, or an enantiomer or a diastereomer thereof. In some examples, the adhesive layer may be surrounded by a temporary liner and a backing.

Some embodiments of transdermal patches include a multi-layer drug-in-adhesive comprising compound 1, or an enantiomer or a diastereomer thereof. In some examples, the multi-layer drug-in-adhesive patch is similar to the single-layer system. The multi-layer system is different, however, in that it adds another layer of drug-in-adhesive, which may or may not be separated by a membrane. In some embodiments of the multi-layer drug-in adhesive, one of the layers is for immediate release of compound 1, or an enantiomer or a diastereomer thereof, and other layer is for control release of compound 1, or an enantiomer or a diastereomer thereof, from a reservoir. In some cases, the multi-layer drug-in-adhesive has a temporary liner-layer. In some embodiments, the multi-layer drug-in-adhesive has a permanent backing. Any suitable release profile of compound 1, or an enantiomer or a diastereomer thereof, from the multi-layer drug-in-adhesive may be selected by the person skilled in the art.

In some embodiments, the transdermal patch may comprise a separate layer that includes or consists of a reservoir comprising compound 1, or an enantiomer or a diastereomer thereof. In some examples, the reservoir comprising compound 1, or an enantiomer or a diastereomer thereof, is a liquid compartment containing compound 1, or an enantiomer or a diastereomer thereof, as a solution, a suspension, or a solid, separated by the adhesive layer. Some embodiments include a reservoir that is totally encapsulated in a shallow compartment molded from a drug-impermeable plastic laminate, with a rate-controlling membrane made of a polymer (e.g., vinyl acetate) on one surface. In some examples, a transdermal patch comprising a reservoir may be protected on one side by a backing layer.

In some embodiments, the transdermal patch may comprise a matrix system. Some matrix system embodiments include a layer of a semisolid matrix comprising a solution or suspension of compound 1, or an enantiomer or a diastereomer thereof. In some embodiments of the matrix system, the adhesive layer in the transdermal patch surrounds the drug layer comprising compound 1, or an enantiomer or a diastereomer thereof, and may partially overlay the drug layer comprising compound 1, or an enantiomer or a diastereomer thereof.

Some embodiments include a transdermal patch designed to release compound 1, or an enantiomer or a diastereomer thereof, over about 12 hours to about 1 month. In some embodiments, about 1 mg to about 1,000 mg of compound 1, or an enantiomer or a diastereomer thereof, is released from the transdermal patch per day. In some examples, about 1-2 mg, about 2-3 mg, about 3-4 mg, about 4-5 mg, about 5-6 mg, about 6-7 mg, about 7-8 mg, about 8-9 mg, about 9-10 mg, about 10-11 mg, about 11-12 mg, about 12-13 mg, about 13-14 mg, about 14-15 mg, about 15-16 mg, about 16-17 mg, about 17-18 mg, about 18-19 mg, about 19-20 mg, about 20-22 mg, about 22-24 mg, about 24-26 mg, about 26-28 mg, about 28-30 mg, about 30-32 mg, about 32-34 mg, about 34-36 mg, about 36-38 mg, about 38-40 mg, about 40-42 mg, about 42-44 mg, about 44-46 mg, about 46-48 mg, about 48-50 mg, about 50-55 mg, about 55-60 mg, about 60-65 mg, about 65-70 mg, about 70-75 mg, about 75-80 mg, about 80-85 mg, about 85-90 mg, about 90-95 mg, about 95-100 mg, about 100-110 mg, about 110-120 mg, about 120-130 mg, about 130-140 mg, about 140-150 mg, about 150-160 mg, about 160-170 mg, about 170-180 mg, about 180-190 mg, about 190-200 mg, about 200-300 mg, about 300-400 mg, about 400-500 mg, about 500-600 mg, about 600-700 mg, about 700-800 mg, about 800-900 mg, about 900-1,000 mg, or about 1 mg, about 5 mg, about 10 mg, about 20 mg, or about 40 mg of compound 1, or an enantiomer or a diastereomer thereof, is released from the transdermal patch per day.

In other examples, the transdermal patch comprising compound 1, or an enantiomer or a diastereomer thereof, is designed to release a therapeutic amount of compound 1, or an enantiomer or a diastereomer thereof, for about 6 hours up to 1 month. In some embodiments, the transdermal patch comprising compound 1, or an enantiomer or a diastereomer thereof, is designed to provide a therapeutic amount of compound 1, or an enantiomer or a diastereomer thereof, for 6-9 hours, about 9-12 hours, about 12-15 hours, about 15-18 hours, about 18-21 hours, about 21-24 hours, about 1-2 days, about 2-3 days, about 3-4 days, about 4-5 days, about 5-6 days, about 6-7 days, about 7-8 days, about 8-9 days, about 9-10 days, about 10-11 days, about 11-12 days, about 12-13 days, about 13-14 days, about 14-15 days, about 15-16 days, about 16-17 days, about 17-18 days, about 18-19 days, about 19-20 days, about 20-21 days, about 21-22 days, about 22-23 days, about 23-24 days, about 24-25 days, about 25-26 days, about 26-27 days, about 27-28 days, about 28-29 days, about 29-30 days, about 30-31 days, about 1-2 months, about 2-4 months, about 4-6 months, about 6-9 months, about 9-12 months, about 1-2 years, about 1 day, about 1 week, about 2 weeks, about 3 weeks, about 4 weeks, about 1 day to about 1 week, about 1-2 weeks, about 2-3 weeks, about 3-4 weeks, or about a month, or about any time period in a range bounded by any of these time periods.

In some embodiments of the present disclosure, compound 1, or an enantiomer or a diastereomer thereof, is formulated as a solid implant, such as a dermal implant, wherein the implant comprises a biodegradable polymer. Some embodiments include a solid implant, comprising a polymer such as ethylene vinyl acetate (EVA). In some examples, the solid implant is soft. In some embodiments, the solid implant is flexible. Some embodiments include solid implants that are rod-shaped.

Implants may be composed of a biodegradable polymer having compound 1, or an enantiomer or a diastereomer thereof, dispersed within the polymer. The biodegradable polymer may degrade or disintegrate over time in the body, releasing compound 1, or an enantiomer or a diastereomer thereof, during the degradation process. Implants may also be composed of a nonbiodegradable.

A biocompatible polymer matrix may be any polymeric material suitable for use in a mammal, including a human being. Examples of biodegradable polymer may include, but are not limited to: polyesters, polyorthoesters, polyphosphoesters, polycarbonates, polyanhydrides, polyphosphazenes, polyoxalates, polyaminoacids, polyhydroxyalkanoates, polyethyleneglycol, polyvinylacetate, polyhydroxyacids, polyanhydrides, copolymers and blends thereof, and the like. In some embodiments, a biodegradable polymer may be a co-polymer of lactic and glycolic acid (e.g. poly(lactide)co(glycolide) (PLGA).

A nondegradable polymer may also be used, including any biocompatible polymer that is substantially intact after release of Compound 1, or an enantiomer or a diastereomer thereof, by a device is substantially complete. The nondegradable polymer may be porous to allow Compound 1, or an enantiomer or a diastereomer thereof, to diffuse out when it comes into contact with bodily fluid. Examples of non-degradable polymers may include, but are not limited to: ethylene vinyl acetate copolymer (EVA), silicone, hydrogels such as crosslinked poly(vinyl alcohol) and poly(hydroxy ethylmethacrylate), acyl substituted cellulose acetates and alkyl derivatives thereof, partially and completely hydrolyzed alkylene-vinyl acetate copolymers, polyvinyl chloride, homo- and copolymers of polyvinyl acetate, polyethylene, polypropylene, crosslinked polyesters of acrylic acid and/or methacrylic acid, alkyl acrylates such as methyl methacrylate or methyl acrylate, polyacrylic acid, polyalkacrylic acids such as polymethacrylic acid, polyvinyl alkyl ethers, polyvinyl fluoride, polytetrafluoroethylene, polycarbonate, polyurethane, polyamide, polysulphones, polystyrene, styrene acrylonitrile copolymers, poly(ethylene oxide), poly(alkylenes), poly(vinyl imidazole), poly(esters), poly(ethylene terephthalate), polyphosphazenes, and chlorosulphonated polyolefins, and combinations thereof.

Some embodiments include a solid implant, such as a dermal, subcutaneous, or intramuscular implant, designed to release compound 1, or an enantiomer or a diastereomer thereof, over about 1 week to about 12 months. In some embodiments, about 1 mg to about 1,000 mg of compound 1, or an enantiomer or a diastereomer thereof, is released from the solid dermal implant per day. In some examples, about 1-2 mg, about 2-3 mg, about 3-4 mg, about 4-5 mg, about 5-6 mg, about 6-7 mg, about 7-8 mg, about 8-9 mg, about 9-10 mg, about 10-11 mg, about 11-12 mg, about 12-13 mg, about 13-14 mg, about 14-15 mg, about 15-16 mg, about 16-17 mg, about 17-18 mg, about 18-19 mg, about 19-20 mg, about 20-22 mg, about 22-24 mg, about 24-26 mg, about 26-28 mg, about 28-30 mg, about 30-32 mg, about 32-34 mg, about 34-36 mg, about 36-38 mg, about 38-40 mg, about 40-42 mg, about 42-44 mg, about 44-46 mg, about 46-48 mg, about 48-50 mg, about 50-55 mg, about 55-60 mg, about 60-65 mg, about 65-70 mg, about 70-75 mg, about 75-80 mg, about 80-85 mg, about 85-90 mg, about 90-95 mg, about 95-100 mg, about 100-110 mg, about 110-120 mg, about 120-130 mg, about 130-140 mg, about 140-150 mg, about 150-160 mg, about 160-170 mg, about 170-180 mg, about 180-190 mg, about 190-200 mg, about 200-300 mg, about 300-400 mg, about 400-500 mg, about 500-600 mg, about 600-700 mg, about 700-800 mg, about 800-900 mg, about 900-1,000 mg, or about 1 mg, about 5 mg, about 10 mg, about 20 mg, or about 40 mg of compound 1, or an enantiomer or a diastereomer thereof, is released from the solid implant per day.

In other examples, the solid implant, such as a dermal, subcutaneous, or intramuscular implant, comprising compound 1, or an enantiomer or a diastereomer thereof, is designed to release a therapeutic amount of compound 1, or an enantiomer or a diastereomer thereof, for about 1 week up to about 12 months. In some embodiments, the transdermal patch comprising compound 1, or an enantiomer or a diastereomer thereof, is designed to provide a therapeutic amount of compound 1, or an enantiomer or a diastereomer thereof, for 1-2 weeks, about 2-3 weeks, about 3-4 weeks, about 4-5 weeks, about 5-6 weeks, about 6-8 weeks, about 8-10 weeks, about 8-12 weeks, about 12-16 weeks, about 16-20 weeks, about 20-24 weeks, about 24-28 weeks, 28-32 weeks, about 32-36 weeks, about 36-40 weeks, about 40-44 weeks, about 44-48 weeks, 48-52 weeks, about 1 month, about 2 months, about 3 months, about 4 months, about 5 months, about 6 months, about 7 months, about 8 months, about 9 months, about 10 months, about 11 months, about 12 months, about 1 year, about 1-3 months about 3-6 months, about 6-9 months, about 9-12 months, about 1-2 years, or any time period in a range bounded by any of these values.

In some embodiments, compound 1, or an enantiomer or a diastereomer thereof, is formulated as a viscous liquid dermal implant. Some embodiments include a gel implant. In some examples, the viscous liquid or gel implant comprises a sterile, biodegradable, non-pyrogenic, viscoelastic, homogenized implant comprising compound 1, or an enantiomer or a diastereomer thereof. Suitable materials may include cellulose derivatives, such as hydroxypropylcellulose, carboxymethylcellulose, biopolymers, such as hyaluronic acid, collagen, etc. Some embodiments of liquid or gel implants that include compound 1, or an enantiomer or a diastereomer thereof, are formulated to a concentration of 20 mg/mL in a physiologic buffer. Some embodiments of the viscous liquid or gel implant are designed to release compound 1, or an enantiomer or a diastereomer thereof, over about 6 hours to about 1 week. In some embodiments, about 1 mg to about 1,000 mg of compound 1, or an enantiomer or a diastereomer thereof, is released from the viscous liquid or gel implant per day. In some examples, about 1-2 mg, about 2-3 mg, about 3-4 mg, about 4-5 mg, about 5-6 mg, about 6-7 mg, about 7-8 mg, about 8-9 mg, about 9-10 mg, about 10-11 mg, about 11-12 mg, about 12-13 mg, about 13-14 mg, about 14-15 mg, about 15-16 mg, about 16-17 mg, about 17-18 mg, about 18-19 mg, about 19-20 mg, about 20-22 mg, about 22-24 mg, about 24-26 mg, about 26-28 mg, about 28-30 mg, about 30-32 mg, about 32-34 mg, about 34-36 mg, about 36-38 mg, about 38-40 mg, about 40-42 mg, about 42-44 mg, about 44-46 mg, about 46-48 mg, about 48-50 mg, about 50-55 mg, about 55-60 mg, about 60-65 mg, about 65-70 mg, about 70-75 mg, about 75-80 mg, about 80-85 mg, about 85-90 mg, about 90-95 mg, about 95-100 mg, about 100-110 mg, about 110-120 mg, about 120-130 mg, about 130-140 mg, about 140-150 mg, about 150-160 mg, about 160-170 mg, about 170-180 mg, about 180-190 mg, about 190-200 mg, about 200-300 mg, about 300-400 mg, about 400-500 mg, about 500-600 mg, about 600-700 mg, about 700-800 mg, about 800-900 mg, about 900-1,000 mg, or about 1 mg, about 5 mg, about 10 mg, about 20 mg, or about 40 mg of compound 1, or an enantiomer or a diastereomer thereof, is released from the viscous liquid or gel implant per day.

In other examples, the viscous liquid or gel implant comprising compound 1, or an enantiomer or a diastereomer thereof, is designed to release a therapeutic amount of compound 1, or an enantiomer or a diastereomer thereof, for about 6 hours up to 1 week. In some embodiments, the viscous liquid or gel implant comprising compound 1, or an enantiomer or a diastereomer thereof, is designed to provide a therapeutic amount of compound 1, or an enantiomer or a diastereomer thereof, for 6-9 hours, about 9-12 hours, about 12-15 hours, about 15-18 hours, about 18-21 hours, about 21-24 hours, about 1-2 days, about 2-3 days, about 3-4 days, about 4-5 days, about 5-6 days, about 6-7 days, or about 1 day, about 2 days, about 3 days, about 4 days, or about any time period in a range bounded by any of these time periods.

A sustained release dosage form, e.g. a viscous liquid, a gel, a solid implant, etc. for injection or implantation, may also be in the form of microparticles, nanoparticles, microcapsules, nanocapsules, colloids, or other forms that are mixtures of solids and liquids. These may be composed of any of the polymers referred to herein, or may be composed of non-polymeric materials. In some embodiments, the sustained release dosage form comprises a polymer. In some embodiments, the sustained release dosage form is polymer free. In some embodiments, the sustained release dosage form comprises nanoparticles or microparticles. In some embodiments, the sustained release dosage form is free of nanoparticles or microparticles. In some embodiments, the sustained release dosage form has less than 10%, less than 5%, less than 1%, or less than 0.1% nanoparticles or microparticles by weight.

Compound 1, or an enantiomer or a diastereomer thereof, may be formulated for oral administration, for example, with an inert diluent or with an edible carrier, or it may be enclosed in hard or soft shell gelatin capsules, compressed into tablets, or incorporated directly with the food of the diet. For oral therapeutic administration, a pharmaceutical composition comprising compound 1, or an enantiomer or a diastereomer thereof, may be incorporated with an excipient (such as dicalcium phosphate) and used in the form of ingestible tablets, buccal tablets, troches, capsules, elixirs, suspensions, syrups, wafers, and the like. Tablets, troches, pills, capsules and the like comprising compound 1, or an enantiomer or a diastereomer thereof, may also contain one or more of the following: a binder; an excipient; a disintegrating agent; a diluent, a lubricant; and a sweetening and/or flavoring agent.

When the dosage unit form of compound 1, or an enantiomer or a diastereomer thereof, is a capsule, it may contain, in addition to materials of the above type, a liquid carrier. Various other materials may be present as a coating, for example, tablets, pills, or capsules may be coated with shellac, sugar or both. A syrup or elixir may contain compound 1, or an enantiomer or a diastereomer thereof, a sweetening agent, methyl and propylparabens as preservatives, a dye and a flavoring agent. It may be desirable for material in a dosage form or pharmaceutical composition to be pharmaceutically pure and substantially nontoxic in the amounts employed.

Many embodiments of the pharmaceutical compositions comprising compound 1, or an enantiomer or a diastereomer thereof, utilize a binder. In certain embodiments, binders are selected from the group consisting of povidone (PVP) K29/32, hydroxypropylcellulose (HPC), hydroxypropylmethylcellulose (HPMC), ethylcellulose (EC), corn starch, pregelatinized starch, gelatin, sugar, gum tragacanth, and acacia.

Various embodiments of the pharmaceutical compositions of compound 1, or an enantiomer or a diastereomer thereof, also include a lubricant. Suitable lubricants include magnesium stearate, stearic acid, sodium stearyl fumarate, calcium stearate, hydrogenated vegetable oil, mineral oil, polyethylene glycol, polyethylene glycol 4000-6000, talc, glyceryl behenate, etc.

In some examples, disintegrating agents in the pharmaceutical compositions include, but are not limited to, agar, calcium carbonate, maize (corn) starch, potato starch, tapioca starch, alginic acid, alginates, certain silicates, and sodium carbonate. Suitable super disintegrating agents include, but are not limited to crospovidone, croscarmellose sodium, AMBERLITE (Rohm and Haas, Philadelphia, Pa.), and sodium starch glycolate.

In certain embodiments, diluents in the pharmaceutical compositions include, but are not limited to, mannitol powder, spray dried mannitol, microcrystalline cellulose, lactose, dicalcium phosphate, tricalcium phosphate, starch, pregelatinized starch, compressible sugars, silicified microcrystalline cellulose, and calcium carbonate.

Some embodiments of the pharmaceutical compositions include sweeteners, flavors, buffering agents, and flavor enhancers to make the dosage form more palatable. Sweeteners include, but are not limited to, fructose, sucrose, glucose, maltose, mannose, galactose, lactose, sucralose, saccharin, aspartame, acesulfame K, and neotame. Common flavoring agents and flavor enhancers that may be included in the pharmaceutical compositions described herein include, but are not limited to, maltol, vanillin, ethyl vanillin, menthol, citric acid, fumaric acid, ethyl maltol, tartaric acid, peppermint, oil of wintergreen, cherry flavoring or orange flavoring.

Some pharmaceutical compositions or dosage forms may be a liquid or may comprise a solid phase dispersed in a liquid. In some embodiments, compound 1, or an enantiomer or a diastereomer thereof, may be formulated for parental or intraperitoneal administration. Solutions of compound 1, or an enantiomer or a diastereomer thereof, as its free base or pharmaceutically acceptable salts can be prepared in water suitably mixed with a surfactant, such as hydroxypropylcellulose. In certain embodiments, a pharmaceutical composition may be a dispersion that can also have an oil dispersed within, or dispersed in, glycerol, liquid polyethylene glycols, and mixtures thereof. Under ordinary conditions of storage and use, a subject dosage form may contain a preservative to prevent the growth of microorganisms. Examples of suitable preservatives include, but are not limited to, benzalkonium chloride, methyl and ethyl parabens, hexetidine, phenyl mercuric salts and the like, and mixtures thereof.

It is believed that compound 1, or an enantiomer or diastereomer thereof, or a subject dosage form may be useful, alone or in combination with other drugs, in the treatment and/or prevention of a wide variety of diseases and disorders, including neurological disorders. Examples of neurological disorders that may be treated, or that may be treated with increased efficacy, by a subject dosage form include, but are not limited to: affective disorders, psychiatric disorders, cerebral function disorders, movement disorders, dementias, motor neuron diseases, neurodegenerative diseases, seizure disorders, schizophrenia, and headaches. Affective disorders that may be treated by pharmaceutical compositions of a subject dosage form include, but are not limited to, depression, major depression, treatment resistant depression and treatment resistant bipolar depression, bipolar disorders including cyclothymia, seasonal affective disorder, mood disorders, chronic depression (dysthymia), psychotic depression, postpartum depression, premenstrual dysphoric disorder (PMDD), situational depression, atypical depression, mania, anxiety disorders, panic disorders, attention deficit disorder (ADD), attention deficit disorder with hyperactivity (ADDH), attention deficit/hyperactivity disorder (AD/HD), bipolar and manic conditions, obsessive-compulsive disorder, an eating disorder, anorexia nervosa, bulimia, obesity or weight-gain, narcolepsy, chronic fatigue syndrome, premenstrual syndrome, substance addiction or abuse, nicotine addiction, psychosexual dysfunction, pseudobulbar affect, and emotional lability. Other disorders that may be treated, or that may be treated with increased efficacy, by a subject dosage form include, but are not limited to: hypertension, scleroderma, Parkinson's disease, dyskinesia associated with Parkinson's disease, cognitive impairment, obesity, diabetes, migraine, memory disorders. A subject dosage form may also be used to treat or prevent any type of pain including, but not limited to, musculoskeletal pain, neuropathic pain, cancer-related pain, acute pain, nociceptive pain, inflammatory pain, arthritis pain, allodynia, etc.

In some embodiments compound 1, or an enantiomer or diastereomer thereof, or a subject dosage form, may be useful, alone or in combination with other drugs, in the treatment and/or prevention of pain, depression, or obesity or weight-gain. Compound 1, or an enantiomer or diastereomer thereof, or a subject dosage form, may also be useful for treating a substance use disorder, wherein compound 1, or an enantiomer or diastereomer thereof, or a subject dosage form, induces fewer withdrawal symptoms than a standard-of-care opioid addiction treatment. Depression may include, but is not limited to, depression, major depression (or major depressive disorder), treatment resistant depression, chronic depression (dysthymia), psychotic depression, postpartum depression, situational depression, atypical depression, mania, anxiety disorders, etc. Compound 1, or an enantiomer or diastereomer thereof, or a subject dosage form, may also be used to treat obesity or weight-gain. Compound 1, or an enantiomer or diastereomer thereof, or a subject dosage form, may also be used to treat schizophrenia. Compound 1, or an enantiomer or diastereomer thereof, or a subject dosage form, may also be used to treat or prevent any type of pain including, but not limited to, musculoskeletal pain, neuropathic pain, cancer-related pain, acute pain, nociceptive pain, inflammatory pain, arthritis pain, allodynia, etc.

In some embodiments, compound 1, an enantiomer or a diastereomer thereof, or a subject dosage form may be used to treat a substance use disorder, and may induce fewer withdrawal symptoms than standard-of-care opioid addiction treatments, such as buprenorphine, naloxone, naltrexone, or naloxone. In some embodiments, the standard-of care abuse medication is buprenorphine. In some embodiments, the standard-of care abuse medication is naloxone. In some embodiments, the standard-of care abuse medication is naltrexone. In some embodiments, the standard-of care abuse medication is naloxone. In some embodiments, the substance use disorder is addiction to a pain medication or an opioid such as carfentanil, oxymorphone, hydromorphone, Percocet, tramadol, meperidine (Demerol), codeine, fentanyl, heroin, morphine, oxycodone, hydrocodone, propoxyphene, methadone, meperidine, nalbuphine, pentazocine, butorphanol, or a combination thereof. In some embodiments, the substance use disorder is addiction to carfentanil. In some embodiments, the substance use disorder is addiction to oxymorphone. In some embodiments, the substance use disorder is addiction to hydromorphone. In some embodiments, the substance use disorder is addiction to Percocet. In some embodiments, the substance use disorder is addiction to tramadol. In some embodiments, the substance use disorder is addiction to meperidine (Demerol). In some embodiments, the substance use disorder is addiction to codeine. In some embodiments, the substance use disorder is addiction to fentanyl. In some embodiments, the substance use disorder is addiction to heroin. In some embodiments, the substance use disorder is addiction to morphine. In some embodiments, the substance use disorder is addiction to oxycodone. In some embodiments, the substance use disorder is addiction to hydrocodone. In some embodiments, the substance use disorder is addiction to propoxyphene. In some embodiments, the substance use disorder is addiction to methadone. In some embodiments, the substance use disorder is addiction to meperidine. In some embodiments, the substance use disorder is addiction to nalbuphine. In some embodiments, the substance use disorder is addiction to pentazocine. In some embodiments, the substance use disorder is addiction to butorphanol.

Addiction is one of the most common mental illnesses, affecting millions of people worldwide. An estimated 21 million Americans age 12 or older (7.8 percent of the population) required treatment for substance abuse in 2016, according to the Substance Abuse and Mental Health Services Administration. The National Institute on Drug Abuse defines addiction as "a chronic, relapsing brain disease that is characterized by compulsive drug seeking and use, despite harmful consequences." Addiction encompasses dependence on alcohol, opioids, and nicotine, among many other substances. Opioid abuse has been labelled an epidemic in the United States and is considered to be a public health crisis. Roughly 21 to 29 percent of patients prescribed opioids for chronic pain misuse them, and between 8 and 12 percent develop an opioid use disorder. Extended opioid intake can cause the human body to develop dependence. Opioid dependence causes withdrawal symptoms, which makes it difficult to stop taking them. Withdrawal is the combination of physical and mental effects that a person experiences after they stop using or reduce their intake of a substance such as alcohol, nicotine, and prescription or recreational drugs. Symptoms of opioid withdrawal include, but are not limited to, anxiety, fatigue, sweating, depression, seizures, hallucinations, restlessness, agitation, diarrhea, nausea, vomiting, increased heart rate, muscle pain, abdominal pain, general discontent, pupil dilatation, photophobia, watery eyes, excessive yawning, goose bumps, and tremor. Current treatments for opioid withdrawal include methadone, buprenorphine, naltrexone and naloxone, but each of these medications has side effects and other deficiencies. Newer treatments for opioid withdrawal, and related conditions, are needed.

We have found that compound 1 shows few if any opioid withdrawal signs in morphine addicted rats, in striking contrast to the withdrawal effects of standard-of-medication naloxone.

The invention claimed is:

1. A method of reducing withdrawal symptoms when reducing or discontinuing use of an opioid, comprising administering compound 1 to a human being in need thereof, wherein compound 1 is represented by the formula:

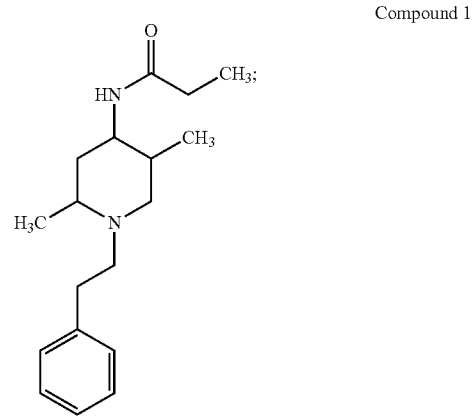 [SMILES: CCC(=O)NC1CC(C)N(CCc2ccccc2)CC1C]

Compound 1 or a pharmaceutically acceptable salt thereof, wherein compound 1 is administered to the human being to reduce withdrawal symptoms when the human being reduces or discontinues use of the opioid.

2. A method of claim 1, wherein compound 1 induces fewer withdrawal symptoms than a standard-of-care opioid addiction treatment.

3. The method of claim 1, wherein the opioid is carfentanil, oxymorphone, hydromorphone, Percocet, tramadol, meperidine, codeine, fentanyl, heroin, morphine, oxycodone, hydrocodone, propoxyphene, methadone, meperidine, nalbuphine, pentazocine, butorphanol, or a combination thereof.

4. The method of claim 2, wherein the standard-of-care opioid addiction treatment is buprenorphine, methadone, naloxone, or naltrexone.

5. The method of claim 2, wherein the standard-of-care opioid addiction treatment is naloxone or naltrexone.

6. The method of claim 1, wherein about 0.01 mg to about 1000 mg of compound 1 is administered daily to the human being in need thereof.

7. The method of claim 6, wherein about 1 mg to about 400 mg of compound 1 is administered daily to the human being in need thereof.

8. The method of claim 1, wherein compound 1 is administered to the human being once, twice, three times, or four times a day.

9. The method of claim 6, wherein compound 1 is released from a sustained release dosage to the human being in need thereof.

10. The method of claim 7, wherein compound 1 is released from a sustained release dosage form to the human being in need thereof.

* * * * *